United States Patent
Alshatwi et al.

(10) Patent No.: US 10,619,249 B2
(45) Date of Patent: Apr. 14, 2020

(54) METHOD FOR PRODUCING NOBLE METAL NANOCOMPOSITES

(71) Applicant: KING SAUD UNIVERSITY, Riyadh (SA)

(72) Inventors: Ali A. Alshatwi, Riyadh (SA); Jegan Athinarayanan, Riyadh (SA); Vaiyapuri Subbarayan Periasamy, Riyadh (SA)

(73) Assignee: King Saud University, Riyadh (SA)

(*) Notice: Subject to any disclaimer, the term of this patent is extended or adjusted under 35 U.S.C. 154(b) by 0 days.

(21) Appl. No.: 16/001,112

(22) Filed: Jun. 6, 2018

(65) Prior Publication Data
US 2018/0282872 A1 Oct. 4, 2018

Related U.S. Application Data

(60) Division of application No. 15/474,760, filed on Mar. 30, 2017, now Pat. No. 10,106,895, which is a
(Continued)

(51) Int. Cl.
C23C 18/44 (2006.01)
H01B 1/02 (2006.01)
(Continued)

(52) U.S. Cl.
CPC ............ C23C 18/44 (2013.01); C01B 32/174 (2017.08); C23C 18/1635 (2013.01); C23C 18/1639 (2013.01); C23C 18/1658 (2013.01); C23C 18/1662 (2013.01); C23C 18/1882 (2013.01); C23C 18/31 (2013.01); B82Y 5/00 (2013.01); B82Y 15/00 (2013.01); B82Y 30/00 (2013.01); B82Y 40/00 (2013.01); H01B 1/02 (2013.01); *Y10S 977/748* (2013.01); *Y10S 977/81* (2013.01); *Y10S 977/847* (2013.01);
(Continued)

(58) Field of Classification Search
CPC ....................................................... H01B 1/02
See application file for complete search history.

(56) References Cited

U.S. PATENT DOCUMENTS

2015/0065601 A1* 3/2015 Alsharaeh ............. C08F 292/00
522/81

OTHER PUBLICATIONS

Xu et al, "Graphene-Metal Particle Nanocornposites," J. Phys. Chem. C, 2008, 112, 19841-19845. (Year: 2008).*
Thesaurus of Agricultural Organisms, Derwent Publications, CRC Press, 1990, p. 96. (Year: 1990).*
Indian Medicinal Plants, Springer-Verlag, 2007, pp. 65-66. (Year: 2007).*

(Continued)

*Primary Examiner* — William D Young
(74) *Attorney, Agent, or Firm* — Richard C. Litman; Nath, Goldberg and Meyer

(57) ABSTRACT

The method for producing noble metal nanocomposites involves reducing noble metal ions (Ag, Au and Pt) on graphene oxide (GO) or carbon nanotubes (CNT) by using *Artocarpus integer* leaves extract as a reducing agent. As synthesized MNPs/GO and MNPs/CNT composites have been characterized using X-ray diffraction (XRD), transmission electron microscope (TEM) imaging, and energy dispersive X-ray spectroscopy (EDX). The TEM images of prepared materials showed that the nanocomposites were 1-30 nm in size with spherical nanoparticles embedded on the surface of GO and CNT. This synthetic route is easy and rapid for preparing a variety of nanocomposites. The method avoids use of toxic chemicals, and the prepared nanocomposites can be used for biosensor, fuel cell, and biomedical applications.

4 Claims, 12 Drawing Sheets

Related U.S. Application Data continuation-in-part of application No. 14/666,307, filed on Mar. 24, 2015, now abandoned.

(51) Int. Cl.

| | |
|---|---|
| *C23C 18/16* | (2006.01) |
| *C23C 18/18* | (2006.01) |
| *C23C 18/31* | (2006.01) |
| *C01B 32/174* | (2017.01) |
| *B82Y 40/00* | (2011.01) |
| *B82Y 5/00* | (2011.01) |
| *B82Y 15/00* | (2011.01) |
| *B82Y 30/00* | (2011.01) |

(52) U.S. Cl.
CPC ........ *Y10S 977/892* (2013.01); *Y10S 977/904* (2013.01); *Y10S 977/92* (2013.01); *Y10S 977/948* (2013.01)

(56) References Cited

OTHER PUBLICATIONS

Iravani, Siavash, "Green Synthesis of Metal Nanoparticles Using Plants", Green Chemistry, 13(10)2638-2650, 2011.

Oyama, Munetaka et al., "Recent Nanoarchitectures in Metal Nanoparticle-Graphene Nanocomposite Modified Electrodes for Electroanalysis", Japan Society for Analytical Chemistry, 30(5), 529-538, May 2014.

Thombre, Rebecca et al., "Studies on Antibacterial and Antifungal Activity of Silver Nanoparticles Synthesized Using *Atocarpus heterophyllus* Leaf Extract", Biotechnol. Bioinf. Bioeng., 2(1), 632-637, 2012.

Wang, Yi et al., "Facile Fabrication of Metal Nanoparticle/Graphene Oxide Hybrids: A New Strategy to Directly Illuminate Graphene for Optical Imaging", The Journal of Physical Chemistry, 115(26), 12815-12821, 2011.

\* cited by examiner

METHOD FOR PRODUCING NOBLE METAL NANOCOMPOSITES

CROSS-REFERENCE TO RELATED APPLICATION

This application is a division of U.S. application Ser. No. 15/474,760, filed Mar. 30, 2017, which is a continuation-in-part of U.S. application Ser. No. 14/666,307 filed Mar. 24, 2015.

BACKGROUND OF THE INVENTION

1. Field of the Invention

The present invention relates to composites, and particularly to a method for producing noble metal nanocomposites that have noble metal nanoparticles (MNP) embedded in a carbon-based substrate of graphene oxide (GO) or carbon nanotubes (CNT).

2. Description of the Related Art

Noble metal nanoparticles have gained remarkable attention due to their excellent physical, chemical and biological properties. On the other hand, carbon-based nano-materials, including graphene oxide (GO) sheets and carbon nanotubes (CNT), are promising supporting materials for noble metal nanoparticles to produce new nanocomposites that can be used in a wide variety of applications because of their distinctive electronic, thermal, and mechanical properties. Currently, the search for synthetic routes for embedding metal nanoparticles on carbon-based materials is a rapidly growing research area in nanoscience and nanotechnology. So far, there have been a number of attempts to carry out a synthesis of noble metal nanoparticles embedded graphene oxide and carbon nanotubes, including chemical reduction, electrochemical, thermal decomposition, ultraviolet and microwave irradiation. However, these methods use hazardous chemicals, high pressure, energy, and temperatures that lead to environmental pollution. Green synthesis is a most promising method for metal nanoparticles (MNPs) synthesis that is considered cost effective, simple, rapid, and eco-friendly, since it does not require toxic chemicals. We have developed a new synthetic route for synthesis of MNPs on GO/CNT. These synthesized samples can be used for biosensors, fuel cells, and biomedical applications.

Thus, a method for producing noble metal nanocomposites solving the aforementioned problems is desired.

SUMMARY OF THE INVENTION

The method for producing noble metal nanocomposites involves reducing noble metal ions (Ag, Au and Pt) on graphene oxide (GO) or carbon nanotubes (CNT) by using *Artocarpus integer* (champedak) leaves extract as a reducing agent. As synthesized MNPs/GO and MNPs/CNT composites have been characterized using X-ray diffraction (XRD), transmission electron microscope (TEM) imaging, and energy dispersive X-ray spectroscopy (EDX). The TEM images of prepared materials showed that the nanocomposites were 1-30 nm in size with spherical nanoparticles embedded on the surface of GO and CNT. This synthetic route is easy and rapid for preparing a variety of nanocomposites. The method avoids use of toxic chemicals, and the prepared nanocomposites can be used for biosensor, fuel cell, and biomedical applications.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
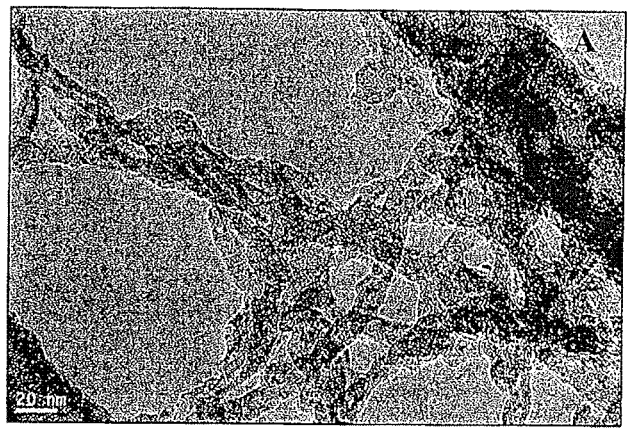
FIG. 1A is a TEM image of a Pt-CNT nanocomposite sample prepared by a method for producing noble metal nanocomposites according to the present invention.
Figure 1B:
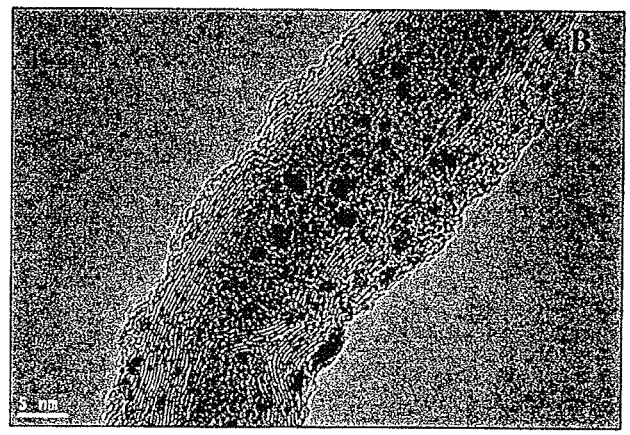
FIG. 1B is a TEM image of the same Pt-CNT nanocomposite sample shown in FIG. 1A, but at higher magnification.
Figure 1C:
FIG. 1C is a TEM image of a Pt-GO nanocomposite sample prepared by a method for producing noble metal nanocomposites according to the present invention.
Figure 1D:
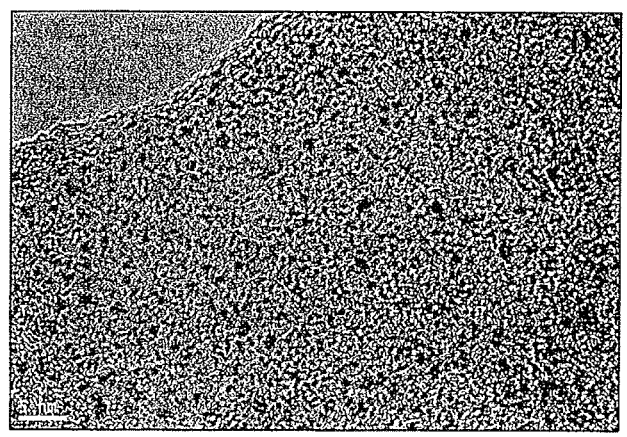
FIG. 1D is a TEM image of the same Pt-GO nanocomposite sample shown in FIG. 1C, but at higher magnification.

The method for producing noble metal nanocomposites involves reducing noble metal ions (Ag, Au and Pt) on graphene oxide (GO) or carbon nanotubes (CNT) by using *Artocarpus integer* (champedak) leaves extract as a reducing agent. As synthesized MNPs/GO and MNPs/CNT composites have been characterized using X-ray diffraction (XRD), transmission electron microscope (TEM) imaging, and energy dispersive X-ray spectroscopy (EDX). The TEM images of prepared materials showed that the nanocomposites were 2-20 nm in size with spherical nanoparticles embedded on the surface of GO and CNT. This synthetic route is easy and rapid for preparing a variety of nanocomposites. The method avoids use of toxic chemicals, and the prepared nanocomposites can be used for biosensor, fuel cell, and biomedical applications.

In the following examples, leaves of *Artocarpus integer* were collected from the Kanyakumari Dist., Tamil Nadu (India). Graphite and CNT were purchased from S.D.Fine, Inida and Sigma, USA respectively. Milli Q water was used throughout the experiments.

Freshly harvested *A. integer* leaves were washed several times with deionized water. About 10 g of leaves were finely chopped and stirred in 200 ml of double-distilled water at 95° C. for 5 min and filtered using a Whatman #1 filter paper to obtain the leaf extract. The filtrate was used as the reducing agent.

Graphene oxide was synthesized from graphite by modified Hummers method. Briefly, 1.0 g graphite powder was dispersed in 24 mL concentrated $H_2SO_4$ under stirring at 0° C. Subsequently, 3.0 g of $KMnO_4$ was added gradually to the mixture and kept in an ice bath. The mixture was stirred for 30 min. The mixture was diluted gradually with 45 mL Milli-Q water. The mixture was re-diluted with 140 mL Milli-Q water and treated with drop-wise addition of 3% hydrogen peroxide. The color of the mixture changed to yellow-brown during the drop-wise addition of $H_2O_2$. The mixture was filtered and washed with HCl solution (5%) and then repeatedly washed with water. Finally, the dark brown graphene oxide (GO) powder was obtained through drying at 50° C. in a vacuum oven.

Functionalized MWCNT (multi-wall carbon nanotubes) were prepared by brutal oxidation using an $H_2SO_4$—$HNO_3$ mixture (3:1 v/v ratio). About 1 g of MWCNT was refluxed with 100 ml of the acid mixture at 120° C. for 6 h. After cooling, the reaction mixture was diluted with 500 ml of Milli-Q water and filtered through vacuum filtration. The obtained product was washed several times with Milli-Q water until the acid was removed. The functionalized MWCNT were used for further experiments.

To obtain platinum nanocomposites, about 20 mg of either GO or the functionalized MWCNT was dispersed in 20 ml Milli-Q water under sonication for 30 minutes. About 5 ml of $1 \times 10^{-2}$ M $H_2PtCl_6$ solution was added drop-wise in GO or the functionalized MWCNT separately under stirring. Following that, the mixture was kept at room temperature for aging and $GO-Pt^+$ or $MWCNT-Pt^+$ complex formation. Excess metal ions of $GO-Pt^+$ or $MWCNT-Pt^+$ mixture were removed by centrifugation. Then 5 ml of the leaves broth (extract) was added to the obtained GO-metal complex or MWCNT-metal complex and mixed well. After 15 minutes incubation, the samples were used for further physico-chemical characterization.

To obtain gold nanocomposites, about 20 mg GO or the functionalized MWCNT was dispersed in 20 ml Milli-Q water under sonication for 30 minutes. About 5 ml of $1 \times 10^{-2}$ M $HAuCl_4$ solution was added drop-wise in GO or the functionalized MWCNT separately under stirring. Following that, the mixture was kept at room temperature for aging and $GO-Au^+$ or $MWCNT-Au^+$ complex formation. Excess metal ions of the $GO-Au^+$ or the $MWCNT-Au^+$ mixture was removed by centrifugation. Then, about 5 ml of the leaves broth (extract) was added to the obtained GO-metal complex or the MWCNT-metal complex and mixed well. After 15 minutes incubation, the samples were used for further physico-chemical characterization.

To obtain silver nanocomposite, about 20 mg GO or the functionalized MWCNT was dispersed in 20 ml Milli-Q water under sonication for 30 minutes. About 5 ml of $1 \times 10^{-2}$ M $AgNO_3$ solution was added drop-wise in the GO or the functionalized MWCNT separately under stirring. Following that, the mixture was kept at room temperature for aging and $GO-Ag^+$ or $MWCNT-Ag^+$ complex formation. Excess metal ions of the $GO-Ag^+$ or the $MWCNT-Ag^+$ mixture were removed by centrifugation. Then, 5 ml of the leaves broth (extract) was added to the obtained GO-metal complex or the MWCNT-metal complex and mixed well. After 15 minutes incubation, the samples were used for further physico-chemical characterization.

Chemical compositions of prepared noble metal nanocomposites were characterized by using Energy Dispersive X-ray analysis (EDAX or EDX). See FIGS. 2A, 2B, 4A, 4B, 6A and 6B. The crystalline nature of the prepared samples was analyzed using X-ray diffraction (XRD). The surface morphology, particle size and diameter of the prepared materials were characterized by using Transmission electron microscope (TEM) (JEOL, JEM2100, Japan). See FIGS. 1A, 1B, 1C, 1D, 3A, 3B, 3C, 3D, 5A, 5B, 5C and 5D.

The crystalline nature of the platinum, gold, and silver nanocomposites was confirmed by the X-ray diffraction analysis. The typical XRD patterns of the prepared samples could be indexed to (1 1 1), (2 0 0), (2 2 0), and (3 1 1) planes of face-centered cubic bulk metallic counterparts.

Figure 2A:
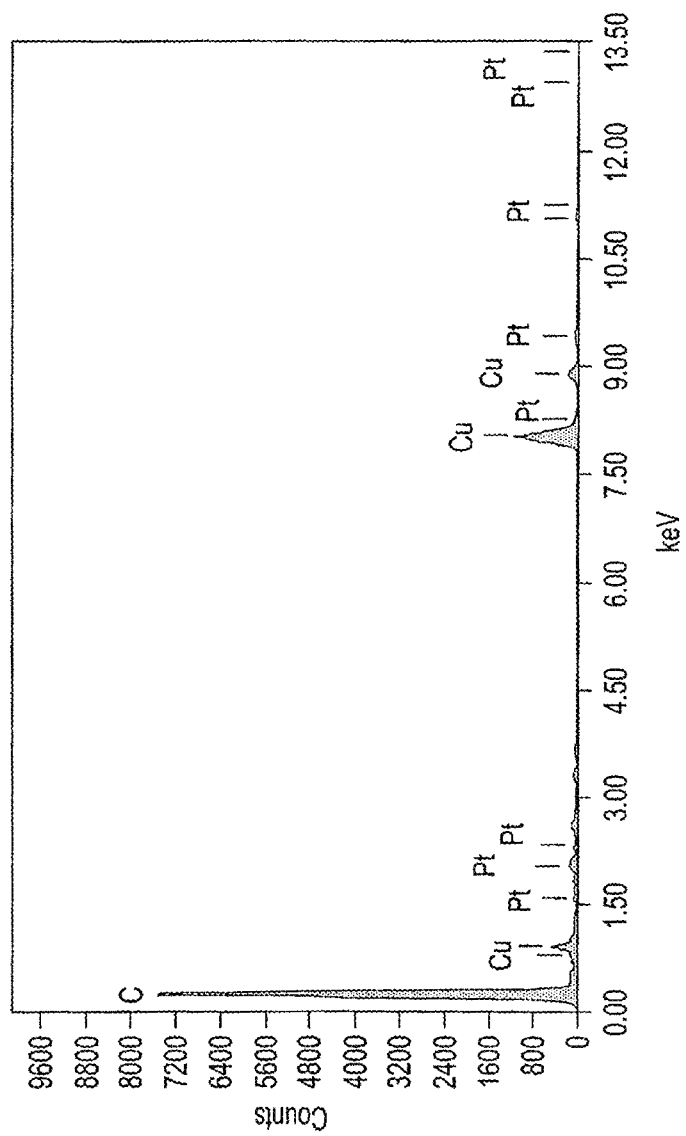
FIG. 2A is an EDX spectrum of the Pt-CNT nanocomposite sample shown in FIGS. 1A and 1B.
Figure 2B:
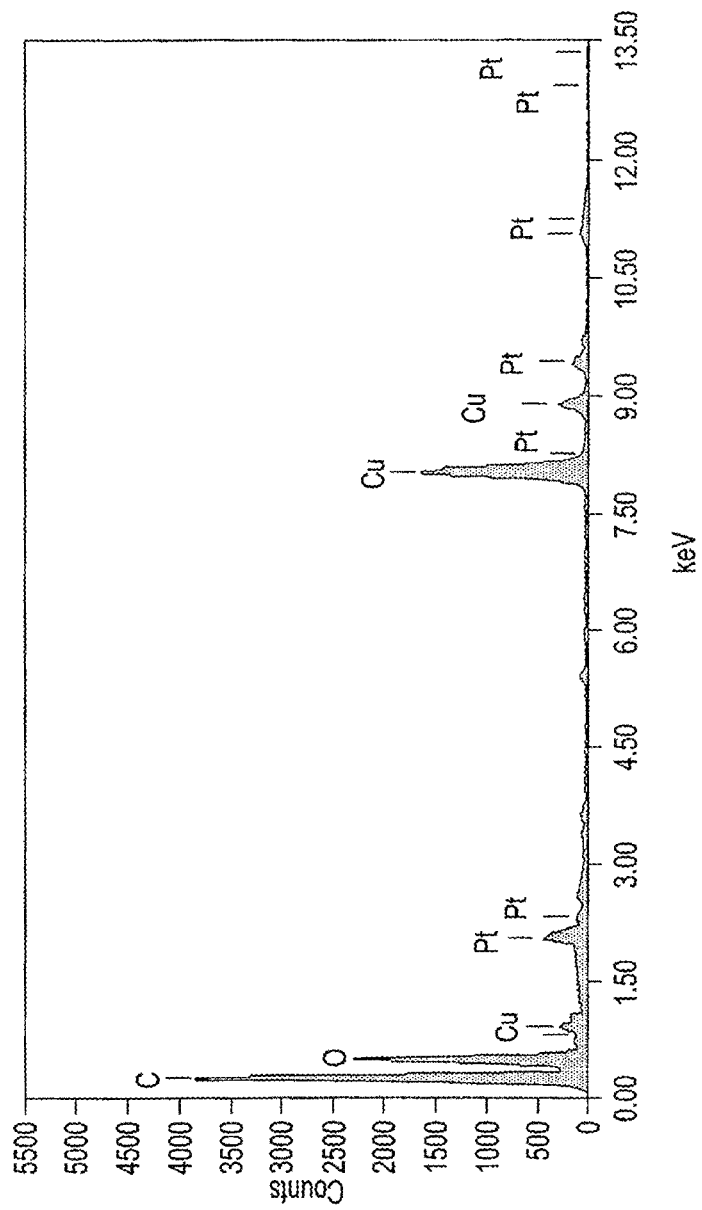
FIG. 2B is an EDX spectrum of the Pt-GO nanocomposite sample shown in FIGS. 1C and 1D.
Figure 3A:
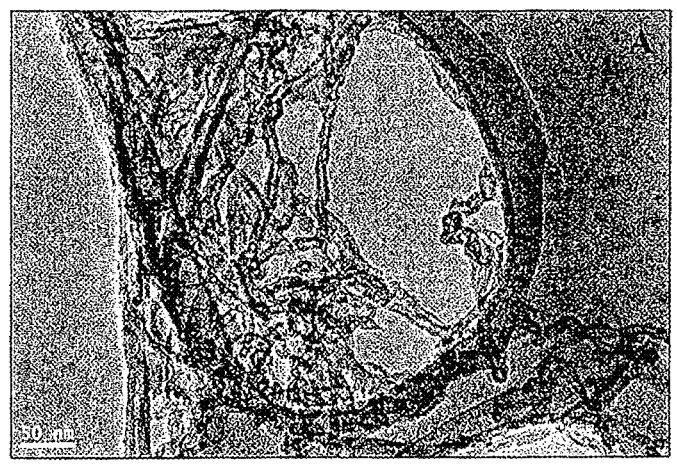
FIG. 3A is a TEM image of an Au-CNT nanocomposite sample prepared by a method for producing noble metal nanocomposites according to the present invention.
Figure 3B:
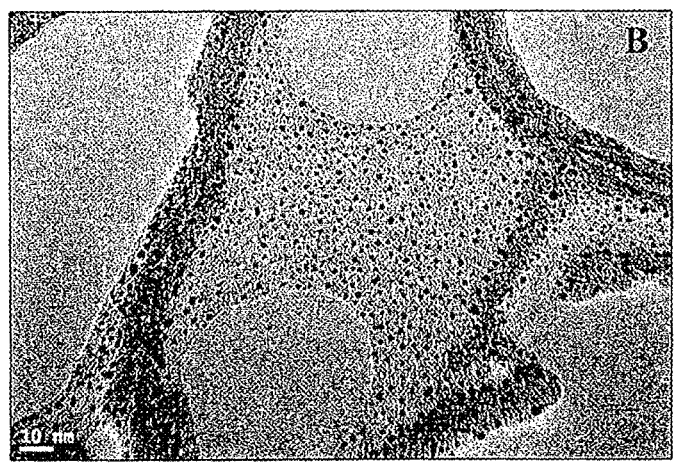
FIG. 3B is a TEM image of the same Au-CNT nanocomposite sample shown in FIG. 3A, but at higher magnification.
Figure 3C:
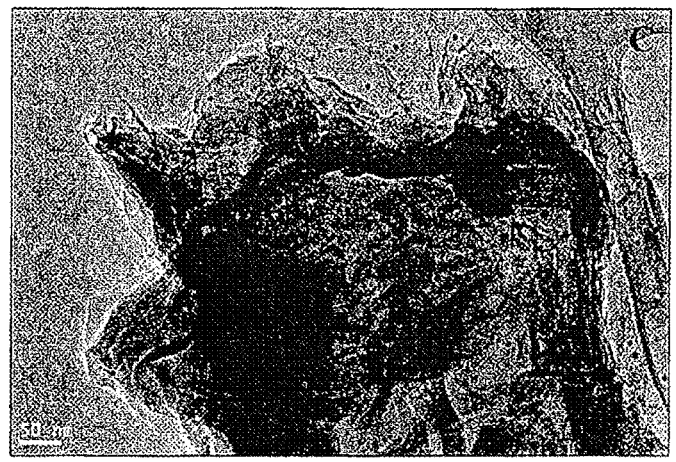
FIG. 3C is a TEM image of an Au-GO nanocomposite sample prepared by a method for producing noble metal nanocomposites according to the present invention.
Figure 3D:
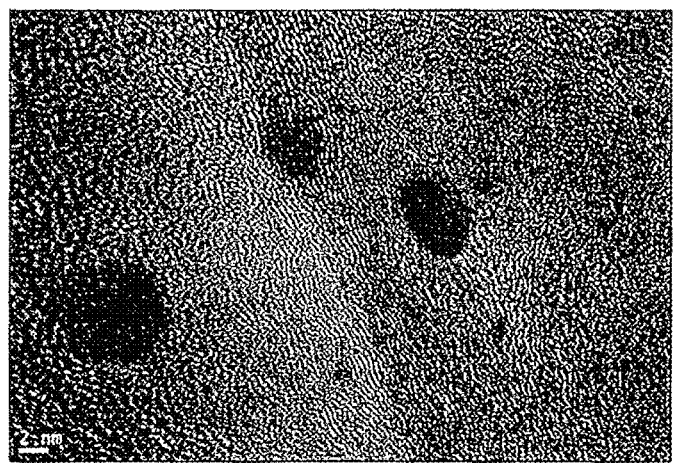
FIG. 3D is a TEM image of the same Au-GO nanocomposite sample shown in FIG. 3C, but at higher magnification.

The morphology and particle size of the prepared platinum nanocomposites were analyzed using transmission electron microscopy. FIGS. 1A-1D show TEM images of the platinum nanocomposites. The platinum nanoparticle size varied between 1-3 nm. The TEM images suggested well dispersed platinum particles on the graphene oxide and carbon nanotube substrates, respectively. The elemental profiles of the prepared nanocomposites were analyzed using TEM with an energy dispersive spectroscopy (EDX) setup. The EDX spectrum (FIG. 2A) for the Pt-CNT nanocomposite showed Pt, C, and Cu peaks, which suggested the presence of platinum nanoparticles on the CNT. FIG. 2B exhibited the Pt, C, O, and Cu peaks, which indicates the presence of platinum nanoparticles on graphene oxide. The Cu peaks correspond to the copper grid used for TEM analysis.

Figure 4A:
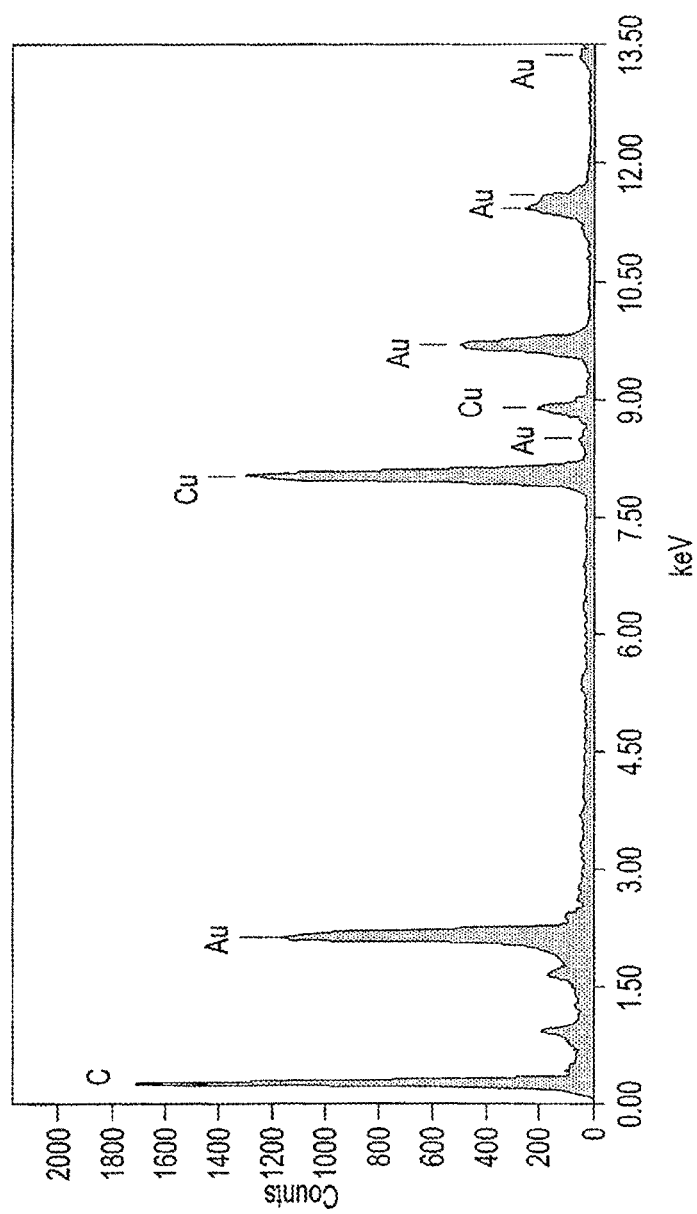
FIG. 4A is an EDX spectrum of the Au-CNT nanocomposite sample shown in FIGS. 3A and 3B.
Figure 4B:
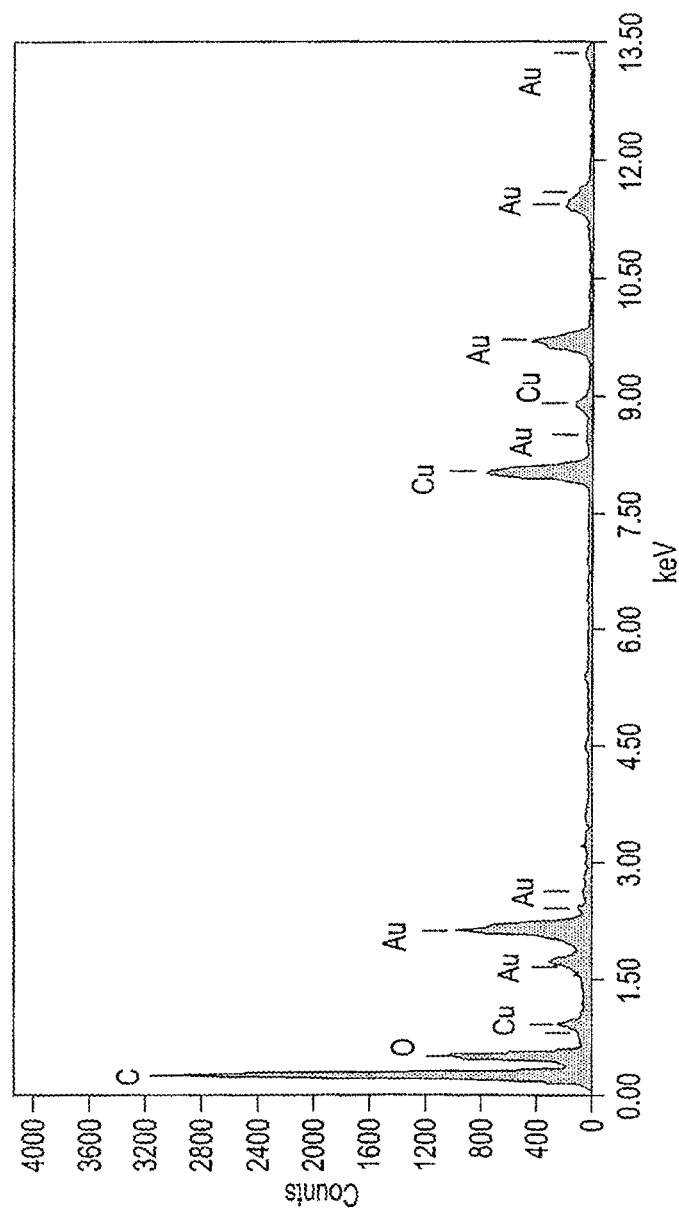
FIG. 4B is an EDX spectrum of the Au-GO nanocomposite sample shown in FIGS. 3C and 3D.
Figure 5A:
FIG. 5A is a TEM image of an Ag-CNT nanocomposite sample prepared by a method for producing noble metal nanocomposites according to the present invention.
Figure 5B:
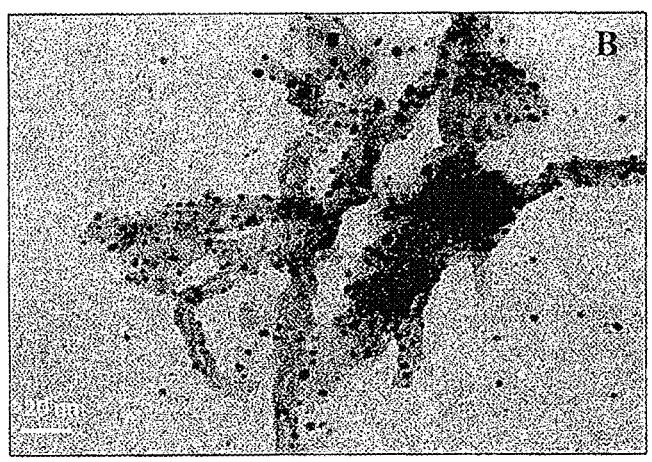
FIG. 5B is a TEM image of the same Ag-CNT nanocomposite sample shown in FIG. 5A, but at higher magnification.
Figure 5C:
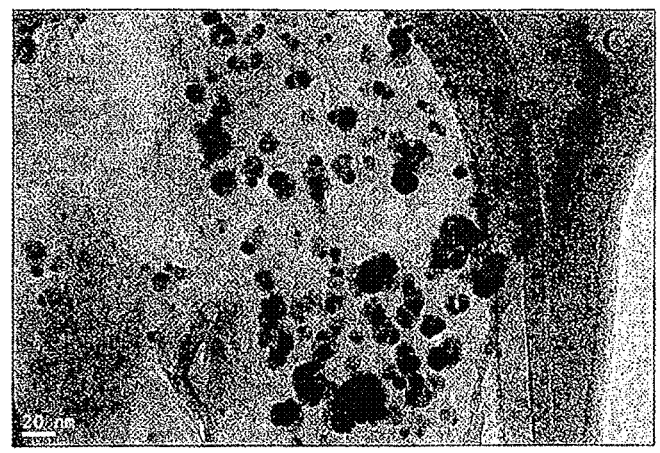
FIG. 5C is a TEM image of an Ag-GO nanocomposite sample prepared by a method for producing noble metal nanocomposites according to the present invention.
Figure 5D:
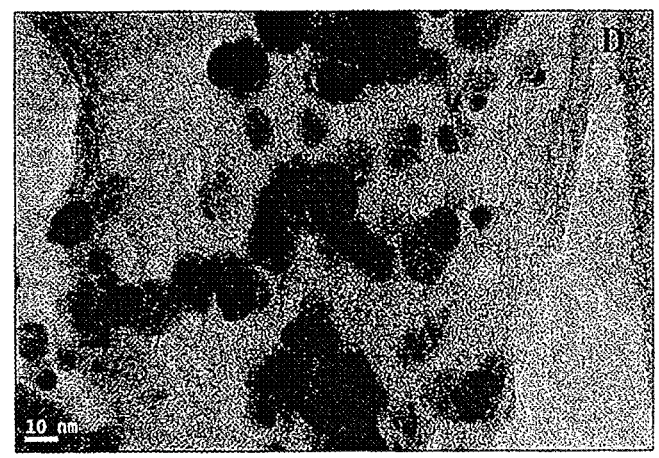
FIG. 5D is a TEM image of the same Ag-GO nanocomposite sample shown in FIG. 5C, but at higher magnification.

The morphology and particle size of the prepared gold nanocomposites were analyzed using transmission electron microscopy. FIGS. 3A-3D show TEM images of the gold nanocomposites. Our results suggested that 10-20 nm spherically shaped gold nanoparticles are uniformly formed on GO and CNT. The elemental profiles of the prepared nanocomposites were analyzed using TEM with an energy dispersive spectroscopy (EDX) setup. The EDX spectrum (FIG. 4A) for the Au-CNT nanocomposite showed Au, C, and Cu peaks, which suggested the presence of gold nanoparticles on the CNT. FIG. 4B exhibited the Au, C, O, and Cu peaks, which indicates the presence of gold nanoparticles (Au) on graphene oxide (C, O). The Cu peaks correspond to the copper grid used for TEM analysis.

Figure 6A:
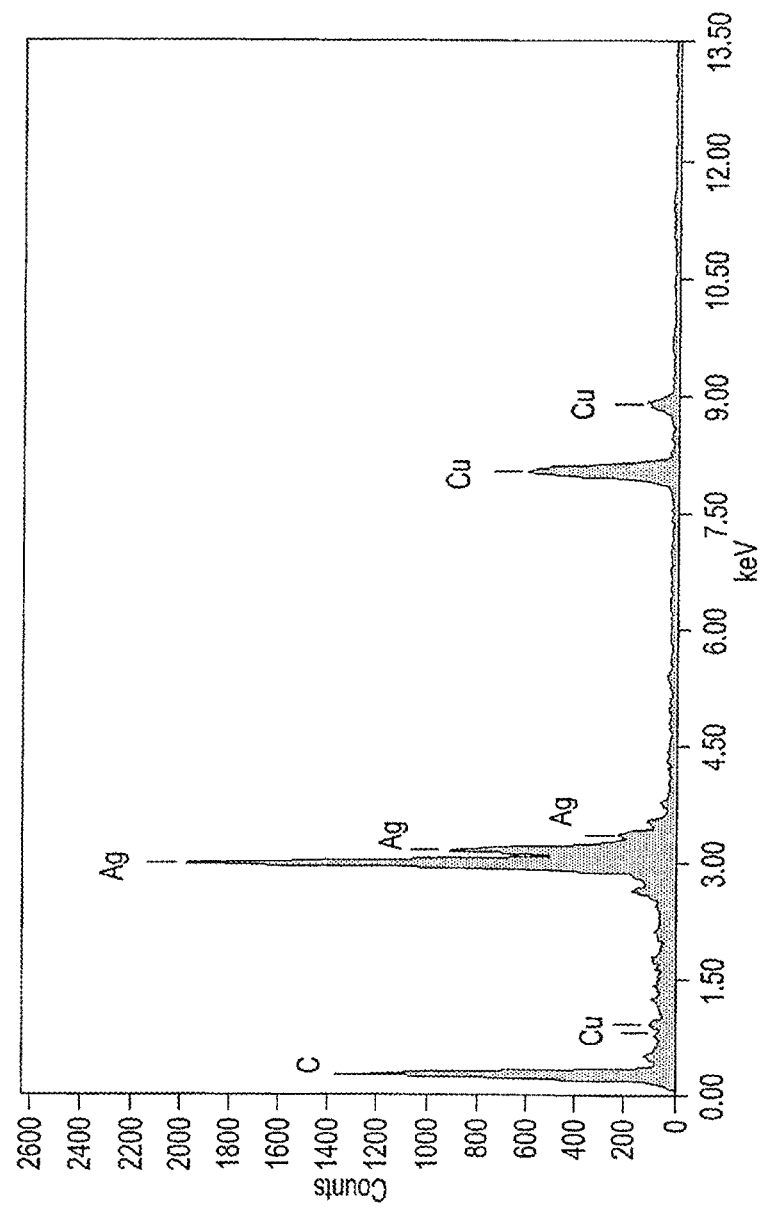
FIG. 6A is an EDX spectrum of the Ag-CNT nanocomposite sample shown in FIGS. 5A and 5B.
Figure 6B:
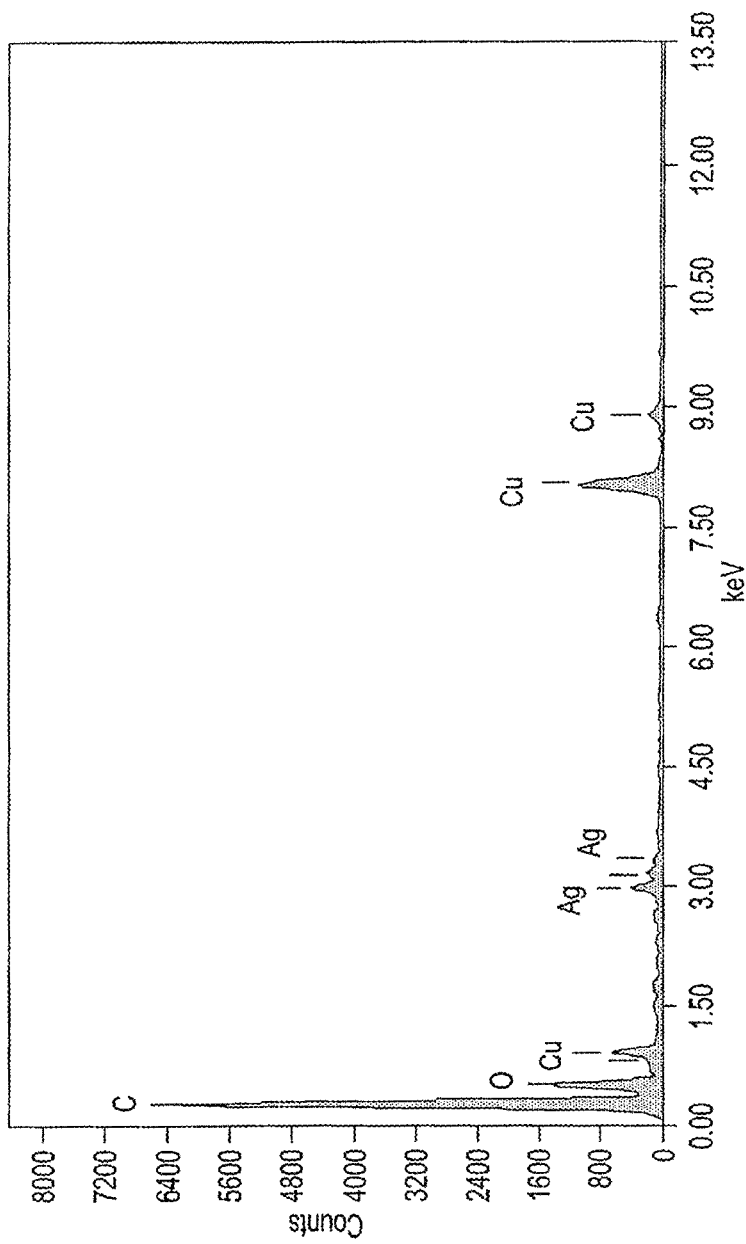
FIG. 6B is an EDX spectrum of the Ag-GO nanocomposite sample shown in FIGS. 5C and 5D.

The morphology and particle size of the prepared silver nanocomposites were analyzed using transmission electron microscopy. FIGS. 5A-5D show TEM images of the silver nanocomposites. The TEM results confirmed that 20-30 nm silver nanoparticles are present on the GO and CNT substrates. The elemental profiles of the prepared nanocomposites were analyzed using TEM with an energy dispersive spectroscopy (EDX) setup. The EDX spectrum (FIG. 6A) for the Pt-GO nanocomposite showed Ag, C, and Cu peaks, which suggested the presence of silver nanoparticles on the CNT. FIG. 6B exhibited the Ag, C, O, and Cu peaks, which indicates the presence of silver nanoparticles on graphene oxide. The Cu peaks correspond to the copper grid used for TEM analysis.

It is to be understood that the present invention is not limited to the embodiments described above, but encompasses any and all embodiments within the scope of the following claims.

We claim:

1. A method for producing noble metal nanocomposites, comprising the steps of:
   preparing an aqueous solution of graphene oxide;
   adding an aqueous solution of a salt of a noble metal to the solution of the graphene oxide to form a complex of the graphene oxide and the noble metal ion in aqueous solution; and
   adding an extract of *Artocarpus integrifolia* leaves to the aqueous solution of the noble metal ion-graphene oxide complex in order to reduce the noble metal ion, thereby forming a composite of nanoparticles of the reduced noble metal embedded in the graphene oxide, wherein the nanoparticles have a particle size between 1 nm and 30 nm, and wherein the noble metal is selected from the group consisting of platinum and gold.

2. The method for producing noble metal nanocomposites according to claim 1, wherein the noble metal is platinum and the nanoparticles of the reduced noble metal have a particle size between 1 nm and 3 nm.

3. The method for producing noble metal nanocomposites according to claim 1, wherein the noble metal is gold and the nanoparticles of the reduced noble metal have a particle size between 10 nm and 20 nm.

4. The method for producing noble metal nanocomposites according to claim 1, wherein the nanoparticles are substantially spherical.

* * * * *